United States Patent [19]

Melinyshyn et al.

[11] Patent Number: 5,389,077
[45] Date of Patent: Feb. 14, 1995

[54] MINIMALLY INVASIVE BODY CAVITY PENETRATING INSTRUMENTS

[75] Inventors: Lev A. Melinyshyn, Buffalo Grove; Edward M. Goldberg, Glencoe; Alexander Poloyko, Morton Grove; David E. Schucart, Homewood, all of Ill.

[73] Assignee: Uresil Corporation, Skokie, Ill.

[21] Appl. No.: 25,983

[22] Filed: Mar. 3, 1993

[51] Int. Cl.⁶ .................. A61M 5/00; A61M 5/178
[52] U.S. Cl. ............................. 604/117; 604/164; 604/264
[58] Field of Search ............ 604/117, 118, 164, 168, 604/158, 264, 272

[56] References Cited

U.S. PATENT DOCUMENTS

| | | | |
|---|---|---|---|
| 4,464,169 | 8/1984 | Semm | 604/26 |
| 4,535,773 | 8/1985 | Yoon | 604/51 |
| 4,624,659 | 11/1986 | Goldberg et al. | 604/121 |
| 4,801,293 | 1/1989 | Jackson | 604/117 |
| 4,869,717 | 9/1989 | Adair | 604/164 |
| 4,944,724 | 7/1990 | Goldberg et al. | 604/118 |
| 5,019,039 | 5/1991 | Anderson | 604/51 |
| 5,066,284 | 11/1991 | Mersch et al. | 604/168 |
| 5,176,697 | 1/1993 | Hasson et al. | 604/191 |
| 5,221,281 | 6/1993 | Klicek | 604/164 |

FOREIGN PATENT DOCUMENTS 4133073  4/1992  Germany ............................. 604/264

*Primary Examiner*—John G. Weiss
*Attorney, Agent, or Firm*—Laff, Whitesel, Conte & Saret

[57] ABSTRACT

An instrument for penetrating into body cavities and potential spaces in preparation for the performance of minimally invasive surgical techniques in which an indicator is provided to assist the surgeon in determining when the instrument is properly placed thereby avoiding injury to vessels and underlying structures in the body cavities and potential spaces.

8 Claims, 2 Drawing Sheets

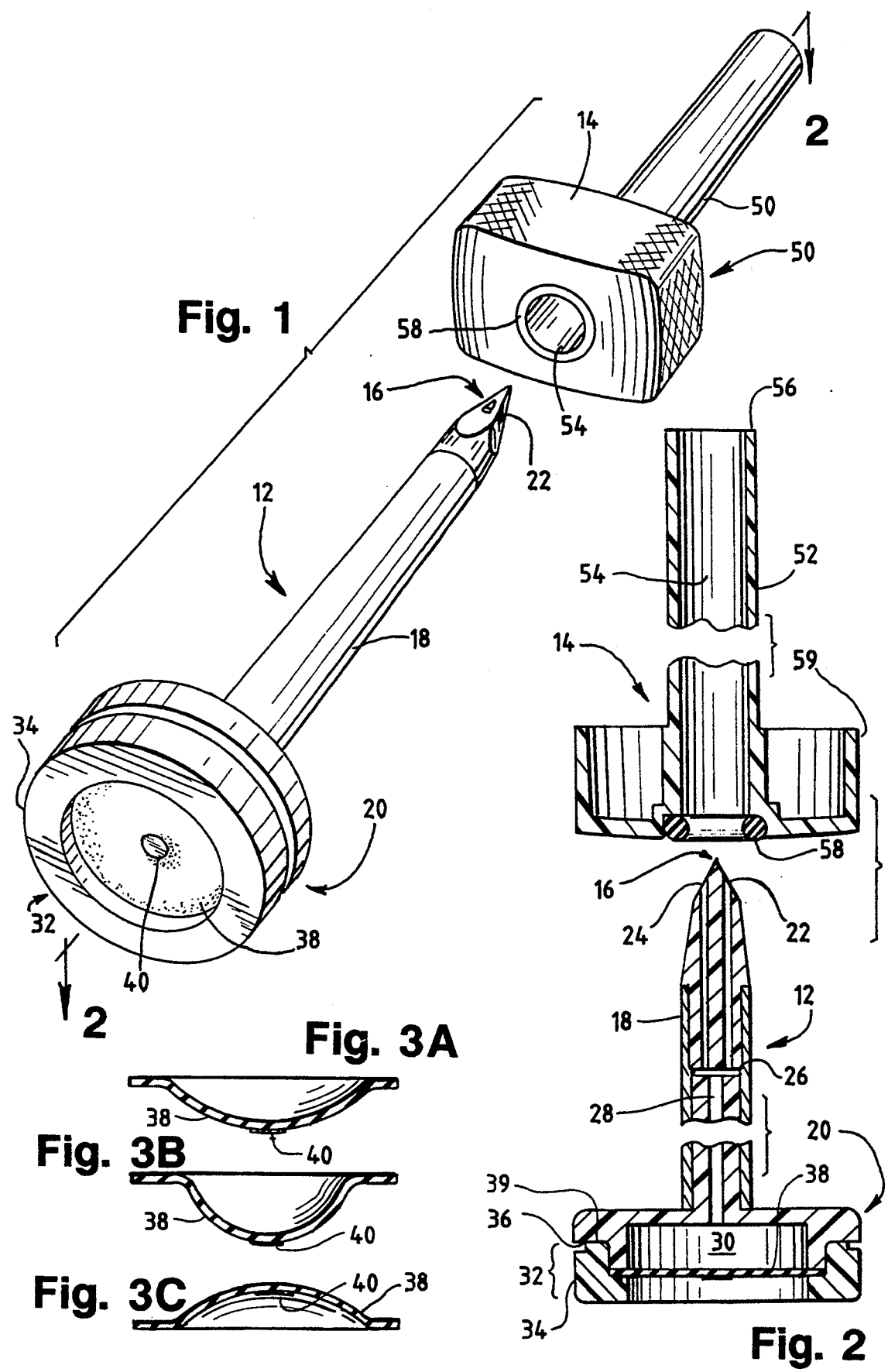

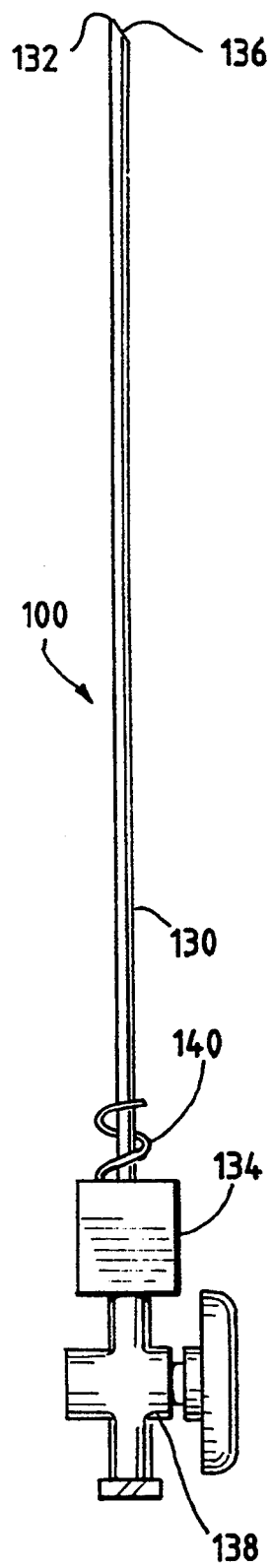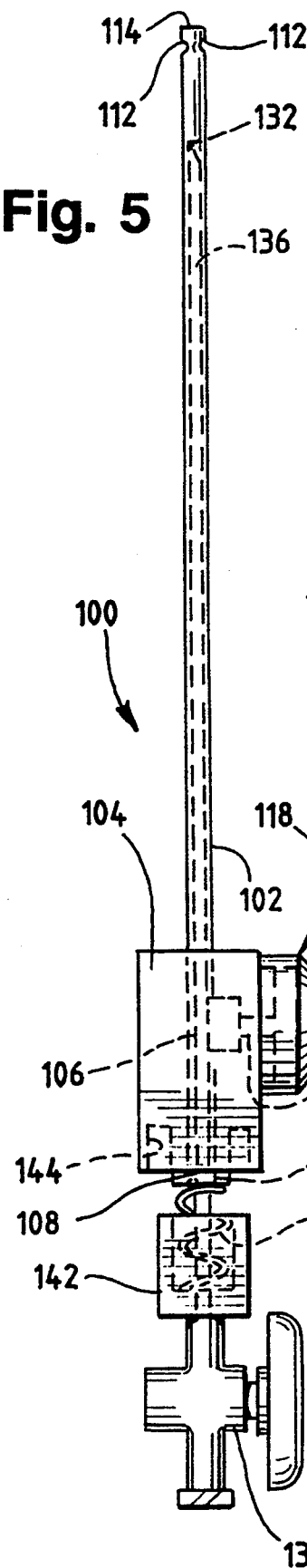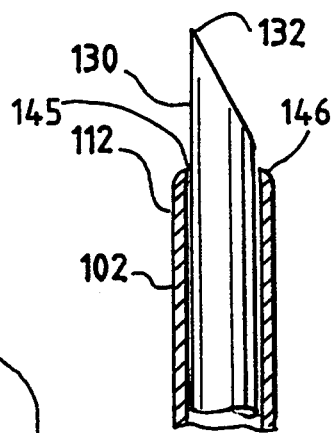

MINIMALLY INVASIVE BODY CAVITY PENETRATING INSTRUMENTS

BACKGROUND OF THE INVENTION

This invention relates generally to instruments for use in minimally invasive surgery, including laparoscopic surgery. More particularly, this invention relates to improved body cavity penetrating instruments for use in minimally invasive surgical techniques, namely insufflation needles and trocar/sleeve assemblies. These improved instruments are adapted to signal proper placement into body cavities (pleural, peritoneal and pericardial) and into potential spaces created in the preplural, properitoneal and prepericarial areas for introducing fluid or mechanical devices.

A host of minimally invasive surgical techniques intended to replace conventional surgical procedures and reduce the trauma of entering the body cavities and potential spaces are currently being developed. These new surgical techniques reduce morbidity and mortality, make it easier to manage the danger of infection, and accelerate recovery and the patient's safe return to full activity.

Current minimally invasive surgical techniques include laparoscopic, endoluminal, perivisceral, endoscopic, thoracoscopic, intra-articular and hybrid approaches. For example, the laparoscopic approach is currently being used in performing cholecystectomy, appendectomy, herniorrhaphy, hysterectomy, vagotomy, pericardiotomy, esophagectomy, hysterectomy, oophorectomy, gastral and bowel resections, nephrectomy, etc.; the thoracoscopic approach is being used in sympathectomy, vagotomy, and excision and closure of bullae and mechanical and chemical pleurodesis and lung resections; and, finally, the intra-articular (arthroscopic) approach is being used in connection with meniscectomy and the remedy of other joint dysfunctions.

An example of a currently widely employed minimally invasive surgical technique is cholecystectomy. In this procedure, as in the other minimally invasive surgical techniques performed in the abdominal cavity, an insufflation needle is inserted into the abdominal cavity through a small incision in the abdominal wall and the peritoneum, and the cavity is insufflated with an insufflating gas, such as carbon dioxide, which is passed through the insufflation needle. The needle is then removed, a trocar/sleeve assembly is inserted at the needle puncture into the insufflated abdomen, the trocar is removed, and an endoscopic camera is inserted into the abdominal cavity through the port of the trocar sleeve. Then, additional incisions are made at strategic locations in the abdominal wall and, under direct visualization, secondary trocar/sleeve assemblies are introduced to provide access for surgical instruments necessary to perform the cholecystectomy.

The insufflation needle and trocar/sleeve assemblies are sharp instruments designed to readily pierce and penetrate into the peritoneal or other body cavity or potential space. In the present state of the art, the sharp tips presented by these devices are shielded by retractable safety devices to prevent injury to underlying structures as the devices are passed into proper position in the body cavities and potential spaces. Nevertheless, when pushed into the body cavities or potential spaces the instrument tips can nick or puncture vessels, organs or other structures contained therein causing serious injury to the patient. On the other hand, if the tip of the instrument is not pushed far enough through the wall of the cavity or space it will not be possible to properly insufflate through the insufflation needle, additional unnecessary trauma may occur and the minimally invasive surgical procedure will be delayed.

Current insufflation needles and trocar/sleeve assemblies do not adequately signal when the devices are properly positioned in the body cavity or potential space in which the minimally invasive surgical procedures are to proceed.

It is therefore an object of the present invention to provide sharp pointed instruments for penetrating body cavities or potential spaces for minimally invasive surgery in which an indication is provided to the surgeon when the instruments are properly placed within the body cavities or potential spaces.

Another object of the present invention is to provide such instruments with means for sensing the pressure within the body cavities or potential spaces.

A further object of the present invention is to provide such instruments with means for giving the surgeon a visual indication of when the instruments enter the body cavities or potential spaces.

Yet another object of the present invention is to provide such instruments with means for giving the surgeon a tactile indication of when the instruments enter the body cavities.

These and other objects and advantages of the invention will become apparent to those skilled in the art upon consideration of the accompanying specification, drawings and claims.

SUMMARY OF THE INVENTION

The present invention is therefore directed to an instrument for penetrating into body cavities and potential spaces in preparation for the performance of minimally invasive surgical techniques. The instrument comprises a cannula which is open at its distal end and adapted to enter a body cavity or potential space as well as an elongated central member sized to fit within the cannula. A seal is provided adjacent the proximal end of the cannula in order to seal against the outer surface of the elongated central member thereby effectively closing the cannula at its proximal end when the central member is in place within the cannula. Finally, an indicator is provided in proximity to the proximal end of the instrument and in fluid communication with the distal ends of the cannula. This indicator signals the pressure in the body cavity or potential space as the distal end of the cannula and central member enter those areas.

The present invention thus solves the need in the art for improved body cavity penetrating instruments for use in minimally invasive surgical techniques which guide the surgeon in quickly, safely and properly positioning the devices in body cavities or potential spaces in which the minimally invasive surgical procedures are to proceed.

BRIEF DESCRIPTION OF THE DRAWINGS

The features of this invention which are believed to be novel are set forth with particularity in the appended claims. The invention, together with its objects and advantages, may be best understood by referring to the following description, taken in conjunction with the accompanying drawings, in which like reference numerals identify like elements in the several figures and in which:

FIG. 1 is a perspective view of a trocar/sleeve assembly in accordance with the present invention, shown before the trocar is engaged in the sleeve;

FIG. 2 is a cross-sectional view of the device of FIG. 1 taken along line 2—2 of FIG. 1;

FIGS. 3A-3C are diagrammatic representations of the indicator membrane of the trocar of FIG. 1 representing various positions of the membrane as the distal end of the assembly passes through the abdominal wall and into the body cavity;

FIG. 4 is an insufflation needle in accordance with the present invention;

FIG. 5 is a cross-sectional view of the insufflation needle of FIG. 4; and

FIG. 6 is an enlarged partial cross-sectional view of the distal end of the insufflation needle of FIG. 4.

DESCRIPTION OF THE PREFERRED EMBODIMENT

Turning now to FIGS. 1 and 2, a trocar/sleeve assembly 10 is illustrated. The assembly includes a trocar 12 and a cannula or sleeve 14.

Trocar 12 has a pyramidal piercing tip 16 at its distal end, a hollow shaft 18, and a handle 20 at its proximal end. Pyramidal piercing tip 16 has longitudinal bores 22 in each of its faces 24. Hollow shaft 18 is undercut at 26 to accept the piercing tip and has a lumen 28 running from undercut 26 (in communication with bores 22) to the proximal end of the trocar where is opens into handle 20.

The trocar may be made of any appropriate biomaterial. In a preferred embodiment, the trocar shaft and handle are made of plastic, such as ABS copolymers, polyoxymethylene-type acetal resin (available commercially as "Delrin") or nylon, and the tip is made of metal such as surgical stainless steel or aluminum and fitted to the plastic shaft by insert molding, gluing, mechanical press-fit, or thread fit.

As best illustrated in FIG. 2, handle 20 has a circular recess 30 onto which a membrane assembly 32 is fitted. Membrane assembly 32 includes a clear plastic cap 34 which is ultrasonically sealed at 36 to the handle to capture elastomeric membrane 38 as shown, over recess 30. In an alternate embodiment, cap 34 may be bonded with adhesive under pressure along the annular surfaces meeting at 39. When the membrane assembly is placed over circular recess 30, the elastomeric membrane entirely covers and seals the proximal end of lumen 28.

The membrane may be made of any soft elastomeric material, such as silicon rubber, latex rubber, urethane or a sufficiently elastic plastisol. A dot 40 which is of a contrasting color to that of the membrane is shown at the center of the membrane. This dot helps the surgeon to detect movement in the membrane. Also, while it is depicted as being located at the proximal end of the trocar, the membrane may be placed at other locations, such as at the edge of handle 20 or along shaft 18.

The central portion 42 of membrane 38 preferably bulges slightly upwardly (toward cap 34) when at rest, as illustrated in FIG. 3A. This slight bulge can be molded into the membrane or achieved by producing a slight positive pressure in the instrument. Membrane 38 will, however, bulge upwardly substantially further when there is a positive pressure in lumen 28, as shown in FIG. 3B. By the same token, a negative pressure in the lumen will cause the membrane to be drawn downwardly toward the proximal end of lumen 28 forming a bulge in the opposite direction, as shown in FIG. 3C.

Sleeve 14, which includes a base 50 and a tube 52, may be made, e.g., of reinforced epoxy, stainless steel, aluminum, or nylon. An annular bore 54 passes through base 50 and tube 52 of the sleeve. The annular bore is sized to firmly but slidably admit trocar 12 which, when fully seated in the sleeve protrudes from the proximal edge 56 of tube 52 so that pyramidal piercing tip 16 is exposed for use in piercing the wall of the body cavity or potential space when the trocar/sleeve assembly is used, as described below. An "O" ring 58 is positioned at the proximal end of the bore to seal against the outer surface of trocar shaft 18 and against appropriate surfaces of other instruments which may later be inserted into the sleeve as a minimally invasive surgical procedure proceeds.

Additionally, base 50 may be provided with means (not shown) for sealing off bore 54 when the trocar is removed. Such sealing means, which do not form part of the present invention, are described, for example, in U.S. Pat. Nos. 4,943,280 and 4,601,710.

The trocar/sleeve assembly is prepared for use by pushing trocar 12 all of the way into sleeve 14. The trocar/sleeve assembly is then grasped firmly by the surgeon with the index and middle fingers extending around the front edge 58 of base 50, on either side of tube 52, and a thumb over membrane 38. Alternatively, the trocar assembly may be gripped with the membrane against the palm of one hand or it may be left exposed for visual observation. Once properly grasped, insertion of the trocar/sleeve assembly begins by urging the pyramidal tip through a small incision or puncture wound previously made in the skin in preparation for the performance of the minimally invasive procedure.

As the trocar tip penetrates the skin, there is little or no movement of the membrane, which remains in the generally plane condition, as illustrated in FIG. 3A. When the tip clears the serous membrane and enters the insufflated cavity, however, the positive pressure in the cavity is immediately transmitted to the membrane, which instantly inflates or bulges up from the proximal end of the handle, as illustrated in FIG. 3B. This inflated membrane thus signals the surgeon that there is no need to insert the trocar/sleeve assembly any further and risk damage to the underlying structures. The signal may be sensed either visually or tactually, depending on whether the surgeon grasps the trocar/sleeve assembly with membrane 38 against his or her hand or leaves the membrane clear for visual observation.

In an alternate embodiment of the invention, an insufflation needle 100 having a tactile and visual indicator is illustrated in FIGS. 4 and 5. The insufflation needle includes an outer cannula 102 mounted to a housing 104. The housing includes a throughbore 106, shown in dotted lines in FIG. 5, which emerges from the housing at proximal face 108, where a seal 110 is provided by a slit latex rubber of other self-sealing elastomeric membrane. Additionally, side ports 112 are located in the outer cannula, near distal tip 114. Ports 112 are positioned about 3 mm. from tip 114 of the outer cannula.

A signal bore 116 is provided in the cannula housing, generally perpendicular to throughbore 106. This signal bore is closed off by a circular elastic membrane 118, which is held in place by a clear window 120 by sandwiching the outer edge of the membrane between corresponding annular surfaces in the housing and the inner surface of the window, in much the same way as described above in connection with membrane assembly 32 of the trocar/sleeve assembly of FIGS. 1-2. Also, window 120 encloses membrane 118, although a hole 122 is provided in the window surface to vent air to the atmosphere such that the membrane can move in response to pressure changes.

An inner cannula 130 provided, having a sharpened tip 132 at its distal end. The inner cannula is firmly mounted at its proximal end in a handle 134 and has a bore 136 which extends from the proximal end of inner cannula 130 to a stopcock 138 at the proximal end of the handle. A recoil spring 140 is mounted on the distal end of the inner cannula handle and enclosed by a tubular collar 140, which is dimensioned to slide into a corresponding annular opening 144 in outer cannula housing 104.

Insufflation needle 100 is assembled for use by inserting inner cannula 130 into housing 104 through "handle" ring 110 and into outer cannula 102 until recoil spring 140 rests against the proximal face 108 of the housing 10. Outer cannula 102 is dimensioned to provide an annular fluid passage 145 between the outer surface of the inner cannula and the inner surface of the outer cannula. In the illustrated embodiment, the inner cannula has an o.d. of about 0.065 inches and the outer cannula has an i.d. of about 0.072 inches, leaving annular passage having a cross-section of about 0.0035 inches.

When the surgeon is ready to begin the insufflation procedure, he or she grasps the fully assembled insufflation needle and thrusts it through the predetermined location in the wall of the body cavity or potential space. Typically, this will be at the umbilicus when minimally invasive surgery is to be performed in the abdominal cavity. The insufflation needle is positioned with the indicator membrane facing upwardly to enable the surgeon to carefully monitor the movement of the membrane as the needle passes into the cavity or space. As the proximal tip of outer cannula 102 meets the wall, recoil spring 140 is compressed and the inner cannula moves forward exposing sharpened tip 132 which punctures the wall. The inner cannula is kept centered to avoid blocking side parts 112 by a rounded lip 146 at the distal end of the outer cannula. The tip of the inner cannula, when deployed, appears as illustrated in FIG. 6. As the device moves across the wall, the fluid pressure at the tip is transmitted through the annular fluid passage to signal bore 116 and membrane 118. Thus, the surgeon grasps the abdominal wall and lifts so that upon entry into the cavity or space a negative pressure is produced and sensed, causing the membrane to depress, as depicted in FIG. 3C, and signalling the surgeon to halt.

Then, insufflation gas is introduced into the cavity by attaching a gas source to stopcock 138 and passing the gas through inner cannula 130. If membrane 118 immediately inflates (FIG. 3B), this indicates that the tip of the insufflation needle is not yet in the cavity or space, (i.e. it is in the facia)—when properly placed, the cavity would become pressurized with the insufflating gas before the membrane would deflect. Under these circumstances, the needle is advanced further into the cavity or space and the membrane observed. Once properly placed, a time lag ensues until the pressure in the insufflated cavity reaches +2 mm. of mercury whereupon the membrane begins bulging outwardly (FIG. 3B).

While particular embodiments of the invention have been shown and described, various changes and modifications may be made therein without departing from the spirit and scope of the invention, and, therefore, it is intended in the appended claims to cover also the changes and modifications within the true spirit and scope of the invention.

What we claim is:

1. An instrument for penetrating into body cavities and potential spaces in preparation for the performance of minimally invasive surgical techniques comprising:
   an outer cannula which is open at its distal end and adapted to enter a body cavity or potential space;
   a central member having a sharp tip at its distal end and being sized to fit within the outer cannula,
   the central member including an outer surface and at least one lumen extending from the sharp tip to the proximal end of the member in which the sharp tip includes at least one orifice in communication with the lumen; and
   means, disposed in proximity to the proximal end of the instrument and in fluid communication with the lumen, for indicating the pressure in the body cavity or the potential space in response to fluid movement at the distal end of the outer cannula.

2. The instrument of claim 1 including means, disposed adjacent the proximal end of the outer cannula, for sealing against the outer surface of the central member.

3. The instrument of claim 1 in which the indicating means comprises an elastomeric membrane sealing off the proximal end of the lumen.

4. The instrument of claim 3 in which a dot of a color contrasting with the color of the membrane is positioned near the center of the membrane.

5. The instrument of claim 3 wherein the membrane bulges upwardly when at rest.

6. The instrument of claim 1 in which the indicating means is mounted to the central member.

7. The instrument of claim 1 in which the indicating means comprises an elastomeric membrane which bulges inwardly and outwardly in response to changes in the pressure at the distal end of the cannula to provide a visual indication of proper placement of the instrument into body cavities and potential spaces.

8. The instrument of claim 1 in which the indicating means comprises an elastomeric membrane which bulges inwardly and outwardly in response to changes in the pressure at the distal end of the cannula to provide a tactile indication of proper placement of the instrument into body cavities and potential spaces.

* * * * *